(12) United States Patent
Hechtle et al.

(10) Patent No.: US 11,192,196 B2
(45) Date of Patent: Dec. 7, 2021

(54) DRILLING TOOL AND METHOD FOR PRODUCING A DRILLED HOLE

(71) Applicant: EMUGE-Werk Richard Glimpel GmbH & Co. KG Fabrik für Präzisionswerkzeuge, Lauf a. d. Pegnitz (DE)

(72) Inventors: Dietmar Hechtle, Pegnitz (DE); Peter Kopton, Kosching (DE)

(73) Assignee: EMUGE-WERK RICHARD GLIMPEL GMBH & CO. KG FABRIK FÜR PRÄZISIONSWERKZEUGE, Lauf A.D. Pegnitz (DE)

( * ) Notice: Subject to any disclaimer, the term of this patent is extended or adjusted under 35 U.S.C. 154(b) by 0 days.

(21) Appl. No.: 16/780,333

(22) Filed: Feb. 3, 2020

(65) Prior Publication Data
US 2020/0246881 A1   Aug. 6, 2020

(30) Foreign Application Priority Data

Feb. 4, 2019   (DE) .......................... 102019102726.8

(51) Int. Cl.
*B23B 51/08*   (2006.01)
*B23D 77/12*   (2006.01)
(Continued)

(52) U.S. Cl.
CPC ............ *B23D 77/006* (2013.01); *B23B 51/08* (2013.01); *B23D 77/12* (2013.01); *B23D 77/14* (2013.01);
(Continued)

(58) Field of Classification Search
CPC ...... B23D 77/00; B23D 77/006; B23D 77/12; B23D 77/14; B23D 2277/36; B23D 2277/60; B23B 51/08
See application file for complete search history.

(56) References Cited

U.S. PATENT DOCUMENTS 2,991,551 A * 7/1961 Fogle .................... B21C 37/298
 72/84
3,592,038 A * 7/1971 Larikka .................. F16L 41/04
 72/325
(Continued)

FOREIGN PATENT DOCUMENTS

DE        3343521 A1 *  6/1985 .............. B21J 5/066
DE   102013017949 B3    12/2014
JP        02180515 A  *  7/1990

OTHER PUBLICATIONS

Search Report received for Hungarian Patent Application No. P2000038, dated Sep. 22, 2020, 1 page.

*Primary Examiner* — Eric A. Gates
(74) *Attorney, Agent, or Firm* — Workman Nydegger

(57) ABSTRACT

The invention relates to a tool for forming a drilled hole (B), comprising a shank that is rotatable or rotates about a tool axis (A), at least one first portion, which is rotatable or rotates about the tool axis (A), for producing and/or widening a drilled hole (B) by chip cutting, and a second portion, which rotates about the tool axis (A), for widening a drilled hole (B) without chip cutting, wherein the second portion is arranged behind the first portion in a direction of advance (V) of the tool. The invention additionally relates to a method for producing a drilled hole (B).

10 Claims, 4 Drawing Sheets

(51) Int. Cl.
  *B23D 77/00*  (2006.01)
  *B23D 77/14*  (2006.01)

(52) U.S. Cl.
  CPC ...... *B23D 2277/36* (2013.01); *B23D 2277/60* (2013.01); *Y10T 29/5107* (2015.01)

(56) References Cited

U.S. PATENT DOCUMENTS

| | | | | |
|---|---|---|---|---|
| 3,762,828 | A * | 10/1973 | Faber | B23D 77/042 |
| | | | | 408/83 |
| 3,884,060 | A * | 5/1975 | Larikka | B23B 51/08 |
| | | | | 72/20.4 |
| 4,116,578 | A | 9/1978 | Gelfand | |
| 4,132,097 | A * | 1/1979 | Ames | B21J 5/066 |
| | | | | 72/325 |
| 4,719,780 | A * | 1/1988 | Ristimaki | B21C 37/298 |
| | | | | 72/126 |
| 5,725,698 | A * | 3/1998 | Mahoney | C22F 1/04 |
| | | | | 148/695 |
| 7,625,292 | B2 * | 12/2009 | Glimpel | B23G 5/06 |
| | | | | 470/199 |
| 8,402,867 | B2 * | 3/2013 | Harif | B23C 5/10 |
| | | | | 82/1.11 |
| 2014/0212234 | A1 | 7/2014 | Sawabe et al. | |
| 2014/0363249 | A1 | 12/2014 | Oka et al. | |

* cited by examiner

DRILLING TOOL AND METHOD FOR PRODUCING A DRILLED HOLE

CROSS-REFERENCE TO RELATED APPLICATIONS

The present invention claims the benefit of priority to German Patent Application No. DE 10 2019 102 726.8, filed Feb. 4, 2019, the entire content of which is incorporated herein by reference.

BACKGROUND OF THE INVENTION

1. The Field of the Invention

The invention relates to a drilling tool and to a method for producing a drilled hole.

2. Background and Relevant Art

Drilling tools that produce a drilled hole by chip cutting are known in the prior art. An overview of the drilling tools that are used is given by the Handbuch der Gewindetechnik and Frästechnik, Editor: EMUGE-FRANKEN, Publisher: Publicis Corporate Publishing, Year of Publication: 2004 (ISBN 3-89578-232-7), referred to in the following simply as the "EMUGE-Handbuch". Known in particular in this case are twist drill bits and stepped drill bits (cf. EMUGE-Handbuch, chapter 7, page 161 ff). A twist drill bit has a uniform diameter over the entire machining region that has helical drilling cutting portions, i.e. secondary cutting portions. A groove in each case extends, in a radially inward direction, along the secondary cutting portion.

In the direction of rotation of the drill bit, the secondary cutting portion is in each case followed by a so-called ridge, which substantially is in the shape of a circular arc in the circumferential direction. The ridge may be provided with a bevel. A stepped drill bit has, arranged in the region of a free end of the stepped drill bit, a first region comprising helical drilling cutting portions, having a first diameter, and has, arranged in succession in the direction of advance, a second region comprising helical drilling cutting portions, that has a second diameter. The second diameter in this case is greater than the first diameter (cf. EMUGE-Handbuch, chapter 7, page 165).

In the case of porous materials, machining with the known drill bits results in the wall of the drilled hole having open pores. Particularly in the case of drilled holes in an engine, such open pores can result in local material overloads or malfunctions during operation of the engine.

Furthermore, known from DE 10 2013 017 949 B3 is a drilled-hole former, in which the drilled hole is produced by tapping, without chip cutting. However, the drilled walls produced do not have a smooth surface, but rather have a corrugated surface.

BRIEF SUMMARY OF THE INVENTION

The object of the present invention is thus to provide a respective device and operational method for tissue treatment, in particular a device that is suitable for treating the drainage system, in particular trabecular meshwork, of the eye, for example in connection with avoiding Glaucoma caused by disturbances in the draining of the eye liquid in the region of the trabecular meshwork of the eye.

It is an object of the invention to provide a tool and a method for producing drilled holes having an improved quality of surface of the drilled-hole wall.

The object of the invention is achieved in respect of the tool by the provision of claim 1 and, in respect of the method, by the provision of claim 9. Expedient designs are given by the dependent claims.

The tool as claimed in the invention for forming a drilled hole comprises a shank that is rotatable or rotates about a tool axis, at least one first portion, which is rotatable or rotates about the tool axis, for producing and/or widening a drilled hole by chip cutting, and a second portion, which rotates about the tool axis, for widening a drilled hole without chip cutting, wherein the second portion is arranged behind the first portion in a direction of advance of the tool. The shank, the first and the second portion are connected to each other in a rotationally fixed manner, or realized as a single piece. In particular, the shank is of a design that is compatible with conventional drill chucks. A drilled hole is first cut by means of the tool as claimed in the invention.

The second portion then widens the cut workpiece, in which the material of the workpiece undergoes deformation at the periphery of the drilled hole. Such a tool is advantageous, in particular, for use in the case of porous materials, in which the pores in the region of the drilled-hole wall are cut open by the first portion, and the irregularities formed by the cut-open pores are then smoothed by the second portion. Such a tool is designed, in particular, to machine metal. The tool may be realized as a single piece or multiple pieces. It may be produced, in particular, from high-speed steel (HSS) or from hard metal. In particular, in a multiple-piece design, cutting portions and/or tapping teeth may be produced, at least partly, from diamond or CBN or similar hard material. In particular, cutting portions and/or tapping teeth may be provided with a coating, e.g. of diamond, CBN or similar.

Preferably, there are one or more cutting portions arranged in the first portion.

Expediently, one of the one or more cutting portions is a secondary cutting portion. In one embodiment, the cutting edge of the secondary cutting portion extends helically around the tool axis, in the first portion. Expediently, arranged in the first portion there may be two or three or four secondary cutting portions that extend parallel to each other, as a helix, around the tool axis. In another embodiment, the cutting edges of the secondary cutting portions are oriented substantially parallel to the tool axis. Expediently, there is a chip groove arranged in front of the cutting edge in the direction of rotation. In this case, direction of rotation, within the meaning of the patent application, is understood to mean the direction in which the tool rotates during forward operation, such that the cutting portions widen the drill hole by chip removal. Arranged behind the cutting edge in the direction of rotation is a ridge, as a cutting heel, which has a clearance angle α. A bevel may be arranged at an edge of the ridge that is opposite the cutting edge.

In one embodiment, at least one of the cutting portions is a primary cutting portion, for cutting and/or widening a drilled hole. The primary cutting portion is arranged, in particular, at the free end of the tool, i.e. in the front region of the first portion in the direction of advance. Expediently, the primary cutting portions are arranged on a conical surface of the tool, and extend radially outward. The number of primary cutting portions corresponds, expediently, to the number of secondary cutting portions. The drilling tool may furthermore have one or more transverse cutting portions, in the front region of the first portion.

In a further embodiment, the second portion is designed such that a pore-free drilled-hole wall is produced.

Expediently, there is at least one forming tooth or forming ridge, in particular precisely one or precisely two or precisely three or precisely four, forming teeth or forming ridges, arranged in the second portion. Such a forming ridge extends, in particular, parallel to the secondary cutting portion(s), i.e. parallel to the tool axis or helically around the tool axis. Expediently, the forming ridge has a roof-shape or sinusoidal shape. In particular, such a forming ridge has a greater maximum radial distance from the tool axis than has/have the cutting portion/s.

In a further embodiment, the first portion has a first diameter, and the second portion has a second diameter, wherein the first diameter is less than the second diameter. A difference between a first and a second diameter may be selected, in particular, in dependence on an anticipated pore size of the workpiece to be machined. The transition from the first to the second diameter is expediently designed as a bevel, having a bevel angle of between 0° and 90°. In a further embodiment, the tool may have a third, or a third and a fourth, portion after the second portion, each further portion expediently having a diameter that is greater than that of the preceding portion. Expediently, with each portion, a drilled pilot hole, or the drilled hole, is widened by 0.005 mm to 0.5 mm, in particular 0.01 mm-0.1 mm.

In one embodiment, the tool is furthermore designed with an internal coolant supply, which expediently extends along, in particular parallel to, the tool axis. Furthermore, the tool expediently has one or more oil grooves that, in particular, extend parallel to the secondary cutting portions. In one embodiment, there may be an oil groove arranged in each case between a cutting portion and a forming ridge that follows in the direction of rotation of the tool, in particular between a bevel and a forming ridge.

The method as claimed in the invention for producing a drilled hole has the following steps: producing and/or widening a drilled hole by chip cutting, widening the drilled hole without chip cutting.

By means of such a method, the drilled hole is first cut, or milled, and subsequently widened by plastic deformation of the drilled-hole wall.

Expediently, a closed, smooth drilled-hole wall is produced from an open-pored drilled-hole wall as the drilled hole is widened.

Expediently, a tool as claimed in the invention is used in the method.

BRIEF DESCRIPTION OF THE DRAWINGS

The invention is explained further in the following on the basis of exemplary embodiments. Reference is also made to the drawing, in which.

DETAILED DESCRIPTION OF THE PREFERRED EMBODIMENTS

Figure 1:
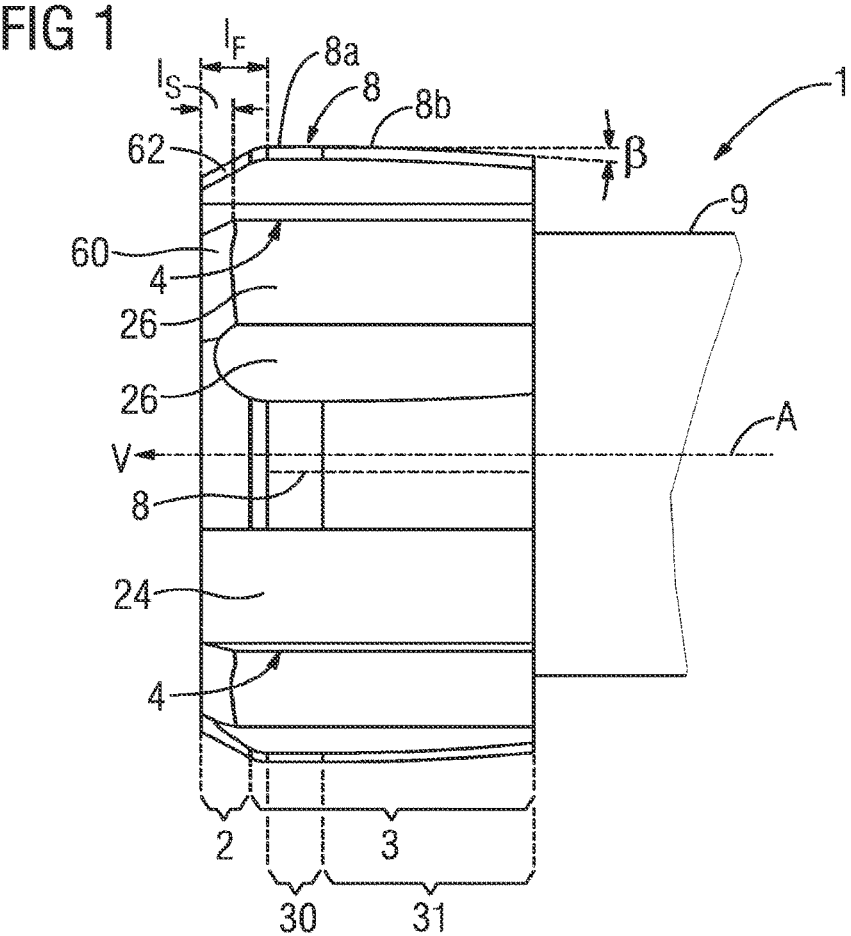
FIG. 1 shows a first embodiment of a tool as claimed in the invention.

FIG. 1 shows a plan view of a handheld device 1 for use in tissue treatment in accordance with the invention, for example for use in in-vivo tissue treatment.

Figure 2:
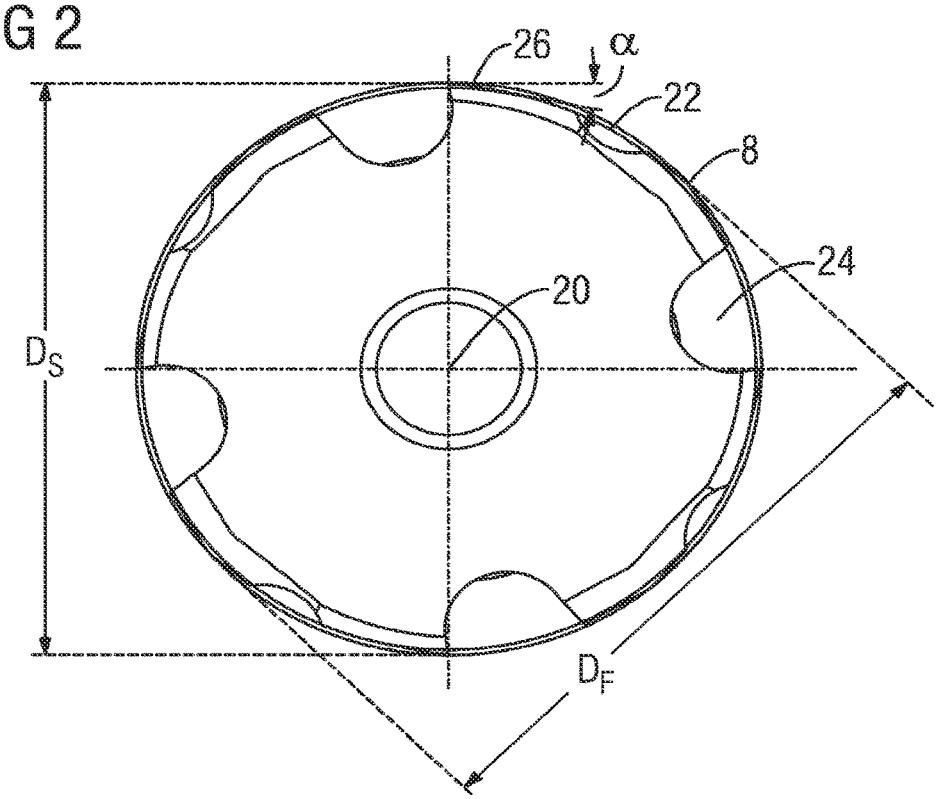
FIG. 2 shows an end view of the first embodiment as claimed in FIG. 1.

FIGS. 1 and 2 show a first embodiment of the tool 1 as claimed in the invention, having a shank 9. The tool 1 has a tool axis A. The tool axis A is arranged centrally in the shank 9. The tool 1 has a free end at the front in a direction of advance V. Located at the free end is the first portion 2 of the tool 1. There is at least one cutting portion 4 arranged in the first portion 2. Here, the cutting portion 4 has a cutting bevel 60, having a length $1_s$. Following the first portion 2, there is a second portion 3. The cutting portions 4 are designed as secondary cutting portions, which here extend parallel to the tool axis. No forming ridges that are capable of widening a drilled hole B are realized in the first portion 2.

Realized here, however, are forming bevels 62, having a length $1_F$, which extend beyond the second portion 2. Here, the length ls is less than the length $1_F$. Realized in the second portion 3, parallel to the secondary cutting portions 4, are forming ridges 8 that, in this embodiment, likewise extend parallel to the tool axis A. In a first region 30 of the second portion 3, the forming ridge 8 is at a greater distance from the tool axis A than in the second region 31. The distance of the forming ridge 8 from the tool axis A in the first region 31 corresponds to the so-called forming diameter $D_F$, which is greater than the so-called cutting diameter $D_S$. In the second region 31, the forming ridge may have a surface that is inclined in relation to the tool axis A, such that a clearance angle $\beta$ is produced. It can be seen from FIG. 2 that there are respectively four forming ridges 8 and four secondary cutting portions 4 arranged uniformly and alternately on the tool 1. In this embodiment, an internal coolant supply channel 20 is routed centrally, parallel to the tool axis A.

Furthermore, this embodiment has oil grooves 22, each running on a back of the secondary cutting portion 4, parallel to the secondary cutting portion 4 and the forming ridge 8. Arranged before the secondary cutting in the direction of rotation, in each case between a secondary cutting portion 4 and a forming ridge 8 and running parallel to them, is a chip groove 24. A ridge 26, which has a clearance angle $\alpha$ opening toward an oil groove 22, runs behind the secondary cutting portion in the direction of rotation. In the embodiment shown, the oil groove 22 has a lesser depth than the chip groove 24.

The tool 1 in the first embodiment is expediently inserted into a drilled pilot hole. When the tool 1 rotates in the direction of advance, the hole is first cut open, by means of the first portion 2, by chip cutting by the cutting portion 4, and then the drilled hole B is widened without chip cutting in the second portion 3, by means of the forming ridge 8, in particular the region of the forming ridge 8 denoted by 8a, which has a distance from the tool axis A that in magnitude is half the forming diameter $D_F$. The cutting portions 4 that extend in the second portion 3 may be functionless. This is the case, in particular, if they have a radial distance from the tool axis A that is less than half of the forming diameter $D_F$. Alternatively, they may also be designed such that the drilled hole B is cut open further in the second portion 3, by means of the cutting portion 4. In this embodiment, the distance of the cutting edge of the cutting portion 4 from the tool axis A must be selected such that only already compressed material in the drilled-hole wall is removed by chip cutting.

Figure 3:
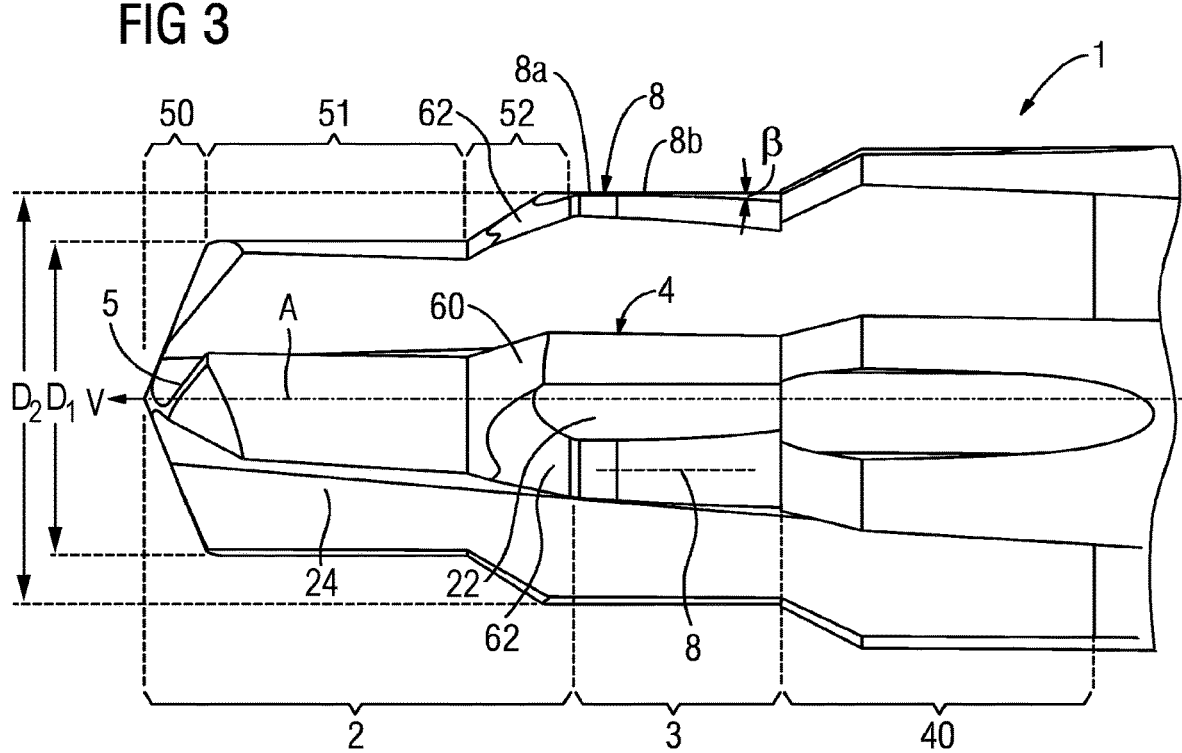
FIG. 3 shows a second embodiment of the tool as claimed in the invention.
Figure 4:
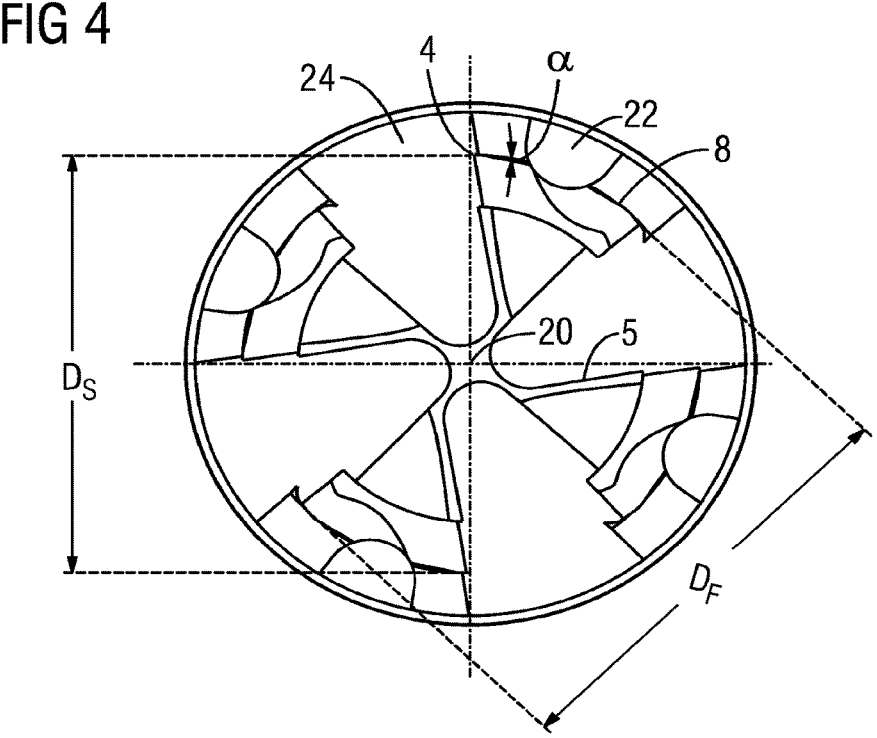
FIG. 4 shows an end view of the second embodiment as claimed in FIG. 3.

FIGS. 3 and 4 show a second embodiment of a tool as claimed in the invention. In this embodiment, the first portion 2 additionally has a primary cutting portion 5, which is arranged in a front region of the first portion 2 in the direction of advance V. Realized in the second portion 3, parallel to the tool axis, are a secondary cutting portion 4, a forming ridge 8, the chip groove 24 and an oil groove 22. The chip groove 24 is realized along the entire secondary cutting portion 4, whereas the oil groove 22 is realized substantially only in the region of the forming ridge 8. In a front region, the forming ridge 8 has a radial distance from the tool axis A that corresponds to half the forming diameter $D_F$. In a region that is behind it in the direction of advance V, the forming ridge 8 is realized with a clearance angle β. This region is denoted by 8b.

The second embodiment additionally has a third region 40, which is behind the second region 3 in the direction of advance V. The third region 40 comprises the secondary cutting portions 4 and the chip grooves 24, as well as the oil grooves 22. As represented, in particular, in FIG. 4, the tool 1 is rotationally symmetrical with respect to the tool axis A, there being a four-fold axis of symmetry present in this design. That is to say four cutting portions and four forming ridges 8 are each arranged with a 90° interval. However, a greater or lesser number of cutting portions and/or forming ridges 8, or a different angular arrangement, is possible.

In the embodiment shown in FIG. 3, the first portion 2 has three sub-regions: a conical first sub-region 50, a cylindrical second sub-region 51, having a first diameter $D_1$, and a third sub-region 52, which comprises a widening of the diameter of the tool 1 and which adjoins the second portion 3. The cutting bevel 60 and the forming bevel 62 are in the sub-region 52. The tool 1 of the second embodiment is suitable for working without separate pilot-hole drilling, or in the case of a drilled pilot hole having a diameter that is significantly less than the first diameter $D_1$.

Figure 7:
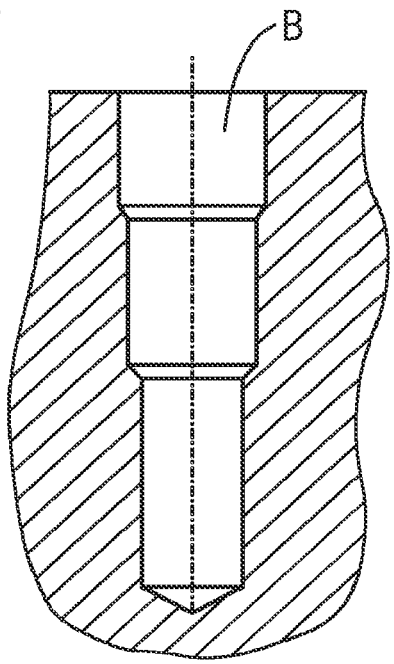
FIG. 7 shows a stepped drilled hole.

The third portion 40 expediently has a diameter that is greater than the forming diameter $D_F$, and that is selected such that only already compressed material in the drilled-hole wall is removed by chip cutting. It is also possible, however, for the diameter of the portion 40 to be greater than the diameter of the already compressed material. In this case, the third portion expediently likewise comprises a forming ridge 8, which further compresses the region of the new drilled-hole wall. The secondary cutting portion 4 in the third portion may be provided with a bevel, in a rear region of the secondary cutting portion. Such a tool may be used, for example, in combination with a drilled hole B that has already been pre-drilled in a stepped manner, as represented in FIG. 7.

Figure 5:
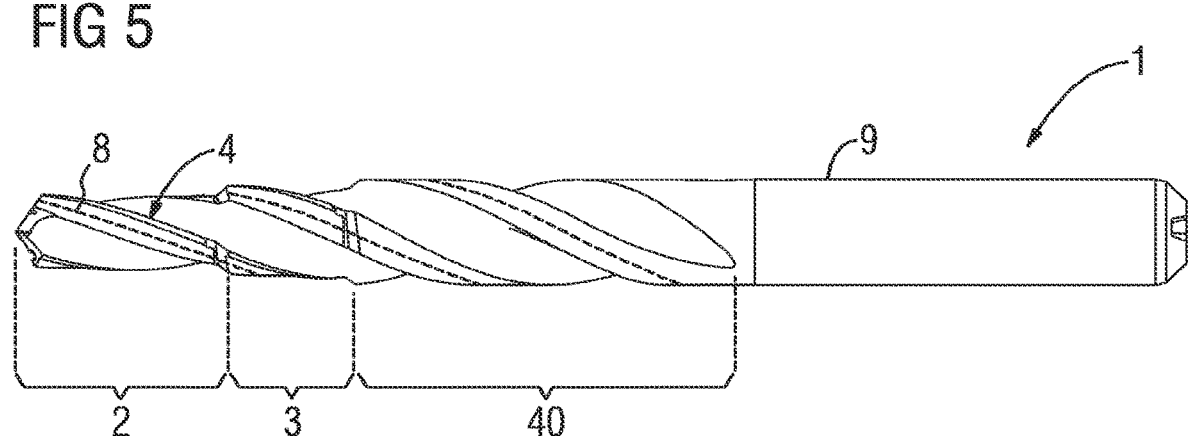
FIG. 5 shows a third embodiment of the tool as claimed in the invention.
Figure 6:
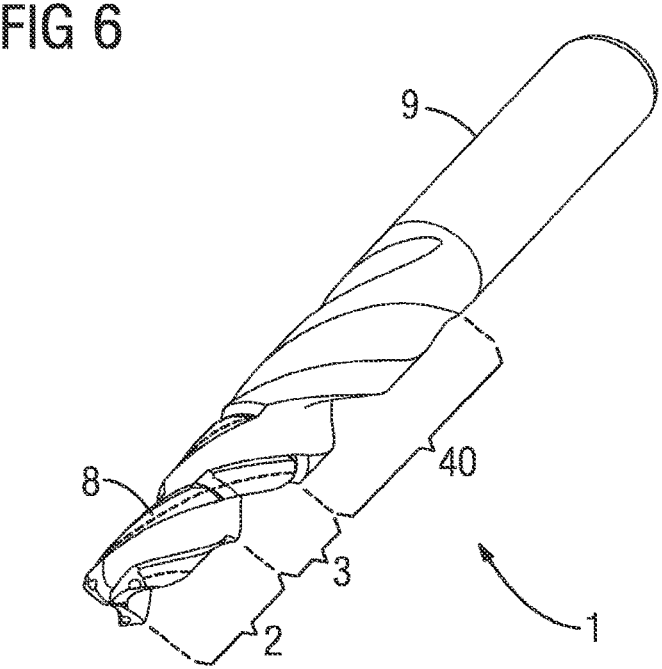
FIG. 6 shows a perspective view of the third embodiment as claimed in FIG. 5.

FIGS. 5 and 6 show views of a third embodiment of the tool as claimed in the invention. The represented tool is based on the second design. In contrast, the tool of the third embodiment has only three cutting portions 4 and three forming ridges 8. Both the forming ridges and the cutting portions are wound helically around the tool axis. However, a greater or lesser number of cutting portions and/or forming ridges, or a different angular arrangement, is possible.

Figure 8:
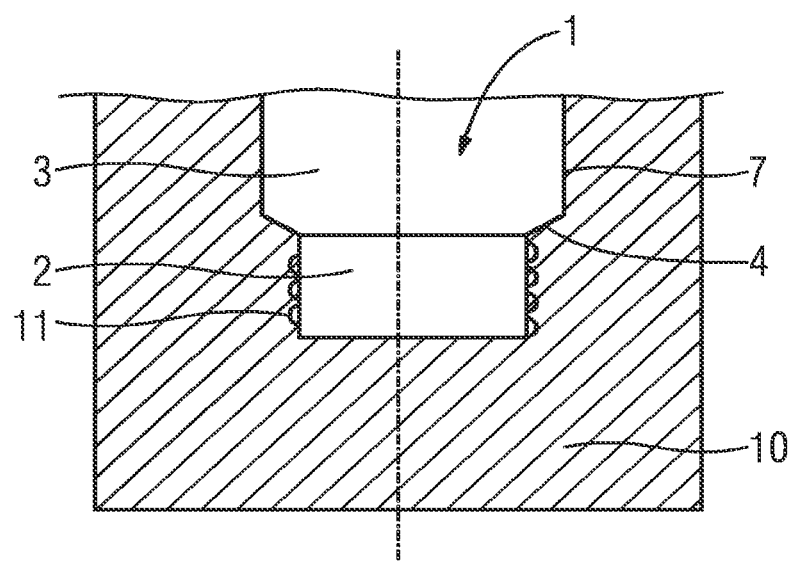
FIG. 8 shows a drilled hole produced by means of a tool as claimed in the invention.

FIG. 8 shows, by way of example, a tool 1 as claimed in the first embodiment, during drilling of a drilled hole B in a workpiece 10. The workpiece 10 has pores 11. The pores 11 are first cut open by means of the cutting portion, in particular the secondary cutting portion 4 in the first portion 2 of the tool 1. The wall of the drilled hole is then widened radially, by plastic deformation, by the second portion 3, by means of a forming tooth 7. The wall of the drilled hole is thereby smoothed. If a diameter of the second portion is appropriately matched to the pore size, the bore wall is pore-free and smooth, as shown.

REFERENCE SIGNS 1 tool
2 first portion
3 second portion
4 secondary cutting portion
5 primary cutting portion
7 forming tooth
8 forming ridge
8a forming ridge with forming diameter
8b forming ridge with clearance angle
9 shank
10 workpiece
11 pore
20 coolant supply channel
22 oil groove
24 chip groove
26 ridge
30 first region
31 second region
40 third portion
42 fourth portion
50 first sub-portion
51 second sub-portion
52 third sub-portion
60 cutting bevel
62 forming bevel
A tool axis
B drilled hole
V direction of advance
$1_F$ forming bevel length
$1_S$ cutting bevel length
α clearance angle
β clearance angle of forming ridge
$D_1$ first diameter
$D_F$ forming diameter
$D_S$ cutting diameter

We claim:

1. A tool for forming a drilled hole (B), comprising:
   a shank that is rotatable about a tool axis (A);
   at least one first portion, which is rotatable about the tool axis (A), for producing and/or widening a drilled hole (B) by chip cutting; and
   a second portion, which rotates about the tool axis (A), for widening a drilled hole (B) without chip cutting;
   wherein the second portion is arranged behind the first portion in a direction of advance (V) of the tool,
   wherein there is/are one or more cutting portions arranged in the first portion,
   at least one of the one or more cutting portions is a secondary cutting portion;
   the at least one secondary cutting portion(s) is/are arranged substantially parallel to the tool axis (A);
   there is at least one forming ridge arranged in the second portion;
   the forming ridge extends substantially parallel to the at least one secondary cutting portion(s); and
   the forming ridge has a clearance angle (β) oriented contrary to the direction of advance (V).

2. The tool as claimed in claim 1, wherein at least one of the cutting portions is a primary cutting portion, for cutting and/or widening a drilled hole (B).

3. The tool as claimed in claim 1, wherein the second portion is designed such that a pore-free drilled-hole wall is produced.

4. The tool as claimed in claim 1, wherein:
the first portion has a first diameter (D1), and the second portion has a second diameter (D2); and
the first diameter (D1) is less than the second diameter (D2).

5. The tool as claimed in claim 1, wherein the tool has one or more oil grooves and/or one or more coolant supply channels.

6. A method for producing a drilled hole (B) with a tool as claimed in claim 1 having the following steps:
producing and/or widening a drilled hole (B) by chip cutting; and
widening the drilled hole (B) without chip cutting.

7. The method as claimed in claim 6, further comprising:
producing a closed, smooth drilled-hole wall from an open-pored drilled-hole wall as the drilled hole (B) is widened.

8. A tool for forming a drilled hole (B), comprising:
a shank that is rotatable about a tool axis (A);
at least one first portion, which is rotatable about the tool axis (A), for producing and/or widening a drilled hole (B) by chip cutting; and
a second portion, which rotates about the tool axis (A), for widening a drilled hole (B) without chip cutting;
wherein the second portion is arranged behind the first portion in a direction of advance (V) of the tool,
wherein there is/are one or more cutting portions arranged in the first portion,
at least one of the one or more cutting portions is a secondary cutting portion;
the at least one secondary cutting portion(s) is/are arranged substantially parallel to the tool axis (A);
the at least one secondary cutting portion(s) having cutting bevels with a length (1s);
wherein the tool comprises a plurality of forming ridges with forming bevels, the forming ridges being arranged parallel to the at least one secondary cutting portion(s);
wherein the forming bevels extend in the first portion and second portion, the forming bevels having a length (1f), the length (1f) of the forming bevels being greater than the length (1s) of the cutting bevels.

9. The tool of claim 8, wherein the forming ridges and the at least one secondary cutting portion(s) are arranged alternately.

10. The tool of claim 8, wherein a forming diameter (DF) of the forming ridge is greater than a cutting diameter (DS) of the at least one secondary cutting portion(s).

* * * * *